United States Patent [19]

Vegesna et al.

[11] Patent Number: 5,262,167
[45] Date of Patent: Nov. 16, 1993

[54] EDIBLE, NON-BAKED LOW MOISTURE CHOLESTYRAMINE COMPOSITION

[75] Inventors: Raju V. K. Vegesna, Parsippany, N.J.; Ashok Y. Gore, Holland; Gerald P. Polli, Valley Forge, both of Pa.

[73] Assignee: BASF Corporation, Parsippany, N.J.

[21] Appl. No.: 630,919

[22] Filed: Dec. 20, 1990

[51] Int. Cl.⁵ .......................... A61K 9/16; A61K 9/20; A61K 31/785; A21D 13/00

[52] U.S. Cl. .................... 424/439; 424/441; 424/464; 424/78.16; 424/501; 426/560; 426/620; 426/622

[58] Field of Search ................ 424/79, 439, 440, 441, 424/78.16; 314/824

[56] References Cited

U.S. PATENT DOCUMENTS

| | | | |
|---|---|---|---|
| 4,778,676 | 10/1988 | Yang et al. | 424/79 |
| 4,790,991 | 12/1988 | Shaw et al. | 424/441 |
| 4,797,288 | 1/1989 | Sharma et al. | 424/476 |
| 4,882,157 | 11/1989 | Yang et al. | 424/440 |
| 4,895,723 | 1/1990 | Auer et al. | 424/79 |
| 4,931,280 | 6/1990 | Wood et al. | 424/439 |
| 4,956,182 | 9/1990 | Bequette et al. | 424/476 |

*Primary Examiner*—Edward Webman

[57] ABSTRACT

A highly palatable, low moisture non-baked cholestyramine composition has cholestyramine in stable admixture with a suitable carrier. The carrier is made up of a grain or flour, sugars and starch binder, and may also contain flavorings, preservative, and an edible oil. The cholestyramine composition should not have more than 11.0% moisture by total weight and the optimal moisture content is not more than 2.0 to 4.0% by weight or lower. The composition may be in the form of coarse granules similar to granola or wheat germ, as well as croutons or chewable tablets which may be consumed without beverages or other food products.

23 Claims, No Drawings

EDIBLE, NON-BAKED LOW MOISTURE CHOLESTYRAMINE COMPOSITION

FIELD OF THE INVENTION

This invention relates to a composition useful in lowering or controlling blood cholesterol levels in humans, and more particularly, to an edible, non-baked cholestyramine composition which is easy to administer and is highly palatable. The invention also relates to a method for lowering or controlling high cholesterol levels in humans utilizing the cholestyramine composition set forth herein.

BACKGROUND OF THE INVENTION

Cholestyramine having the following general formula:

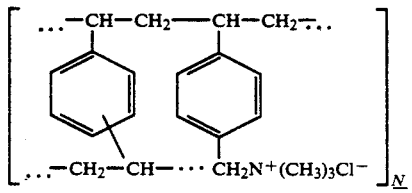

has proven highly efficacious in treating individuals with hypercholesteremia, also known as high blood cholesterol level. This medication is often administered to patients through prescribed dosages on a daily basis, e.g. 4 grams 1-6 times daily, and is often part of an overall regimen which includes a low fat diet and regular exercise. Individuals undergoing cholestyramine treatment have often shown significant reductions in their serum cholesterol levels over time, along with lower incidences of atherosclerosis and other related coronary ailments. For these and other reasons, cholestyramine is often the drug of choice for physicians.

Unfortunately, cholestyramine has an extremely unpleasant taste, characterized by amine, as well as an excessively dry, grimy mouth-feel. Numerous formulations have been provided in an attempt to mask these unpalatable characteristics of the drug. Nougat bars and candy-based formulations, for example, are well known in the art. These products, however, often have a pungent sweetness and an undesirable aftertaste. Furthermore, these preparations often exhibit a high degree of plasticity or gumminess. As a result, many patients who have been prescribed up to four daily dosages or more of one of these cholestyramine-based formulations will often opt to discontinue therapy, further in light of the drug's constipating effect.

Extremely fine powders have also been employed as a vehicle with cholestyramine. These formulations are often mixed with flavorings and colorings and are administered with a beverage such as orange juice. However, cholestyramine, while hydrophilic, is normally insoluble in water, and so many of the undesirable side effects associated with other formulations, e.g. dryness and grittiness, are not significantly reduced with these powdered preparations.

Many of the cholestyramine-based compositions available today may have too high a moisture or water content to be sufficiently palatable. Thus, there presently exists a need for a cholestyramine composition, relatively low in moisture content, which is useful in the treatment of individuals with high cholesterol levels which can be easily administered and which is much more pleasant-tasting than those formulations presently available.

OBJECTS OF THE INVENTION

It is therefore an object of the present invention to provide an improved cholestyramine composition for treatment of individuals with high cholesterol levels.

It is a further object of the invention to provide an improved cholestyramine formulation which is more palatable and pleasant-tasting than those formulations currently available in the art.

Another object of the present invention is to provide a non-baked cholestyramine composition with a relatively low moisture content which is highly palatable and easily ingested.

Still a further object of the invention is to provide a cholestyramine composition in the form of relatively coarse, granola-like granules, croutons, or chewable tablets.

A further object of the invention is to provide a improved method for lowering or controlling blood cholesterol levels which comprises administering an improved and better-tasting cholestyramine composition.

SUMMARY OF THE INVENTION

These and other objects of the invention are achieved by providing an edible, non-baked composition useful for lowering or controlling blood cholesterol levels in humans which comprises cholestyramine in stable admixture with a suitable carrier such that the final composition has a moisture or water content which preferably does not exceed about 11.0% by total weight, more preferably about 4.0%, and most preferably about 2.0%. It has now been discovered that a cholestyramine composition with a relatively low moisture content improves the mouth-feel, consistency and taste of the aforesaid composition. Preferably, the suitable carrier will be a grain or flour-based product, further comprising one or more sugars as well as a starch binder.

In one preferred embodiment of the invention the composition comprises on a weight basis about 7.0 to about 20.0% of one or more grain-based products, about 40.0 to about 50.0% of one or more sugars, about 0.5 to about 3.0% of one or more flavorings, about 5.0 to about 10.0% of starch binder, about 25.0 to about 35.0% cholestyramine, and about 0.1 to about 1.0% of a food preservative, and having a moisture content of from about 2.0 to about 4.0%. In each of the embodiments of the invention, the total weight percentages of all constituents, including the moisture content, will equal 100%. All weight percentages expressed herein are based on the total weight of the final, dry composition, unless otherwise specified.

In another preferred embodiment of the invention, an edible oil is utilized and the final composition comprises on a weight basis from about 7.0 to about 20.0% of one or more grain-based products and has about a 2.0 to about 4.0% moisture content. In addition this embodiment has about 30.0 to about 40.0% of one or more sugars, about 0.5 to about 2.5% of one or more flavorings, about 5.0 to about 10.0% of starch binder, about 20.0 to about 30.0% cholestyramine, and about 0.1 to about 1.0% of a food preservative as well as about 10.0 to about 15.0% of an edible oil.

The cholestyramine composition according to the invention may be packaged, marketed and ingested in suitable dosage form. Typically, an actual dosage of the composition will weigh from about 10.0 to about 17.0 grams and contain about 4.0 grams of cholestyramine per dosage. The actual quantity and weight percentage of cholestyramine may of course vary, depending upon the prescribed unit dosage as well as the actual quantity and weight percentages of the other constituents utilized per dose.

As part of the invention, an improved method of lowering or controlling blood cholesterol levels is also provided. This method involves administering a therapeutically effective dosage of one of the improved cholestyramine compositions set forth herein at a regular interval.

DETAILED DESCRIPTION OF THE PREFERRED EMBODIMENTS

The cholestyramine composition according to the invention comprises cholestyramine in stable admixture with a suitable carrier, the composition being relatively low in moisture. The total moisture content of the final composition should preferably not exceed about 11.0% by weight, more preferably about 4.0%, and most preferably about 2.0%. It is desirable that the aforesaid suitable carrier be a grain or flour-based product with one or more sugars and an acid hydrolyzed starch binder.

The grain or flour-based products may be selected from, for example, raw or processed wheat, oats, corn, bran products and their flours, as well as other grain products known in the art. Whole grains and their flours are preferred, and a combination of rolled oats and oat bran is particularly desirable. The bran may be utilized because it adds important dietary fiber, and further because of its binding effect on cholesterol.

The one or more sugars which are preferably employed in the composition may be selected from the numerous types of simple and complex sugars and sugar substitutes, including mono-, di-, oligo- and polysaccharides, both natural and synthetic, which are available to those skilled in the art. One or more simple sugars may be utilized as sweetening agents. Other types of sugars, e.g. complex sugars, may be utilized to improve the texture, e.g. crunchiness, of the composition. Honey and table sugar or sucrose are contemplated, for example, while fructose powder is especially preferred as a sweetening agent. The more complex soy polysaccharide is also particularly desirable because of the crunchy texture it imparts to the final composition.

An acid hydrolyzed starch binder is also desirable as part of the carrier because of its ability to fine coat the particles of cholestyramine and thereby mask the drug's undesirable taste. Pregelatinized starch marketed under such tradenames as STARCH 1551, ULTRAPURE STARCH, and STARCH TENDER GEL C are preferred, with STARCH TENDER GEL C being particularly preferred.

In one especially desirable embodiment of the invention, the composition comprises one or more grain or flour-based products, one or more sugars, starch binder, and in addition, one or more flavoring agents ad one or more food preservatives, in addition to the cholestyramine.

The flavoring agents may be utilized for additional taste appeal. One or many of the flavoring agents available to those skilled in the art may be added to the composition, depending on individual taste preference. Preferred flavorings include cinnamon, vanilla extract or a combination thereof.

Food preservatives can extend the shelf life of the final cholestyramine composition, and may include, for example, potassium sorbate. Other preservatives known in the art may also be employed.

The heretofore described especially desirable embodiment will most preferably contain about 15.5% to about 16.5% of a grain or flour-based product, most preferably a combination of rolled oats and oat bran in a ratio of approximately 1.2:1.1; about 40.0% to about 45.0% of one or more sugars, most preferably fructose powder and soy polysaccharide; about 1.5 to about 2.5% of one or more flavorings, preferably a combination of cinnamon and vanilla extract; about 8.0 to about 10.0% of starch binder, preferably pregelatinized starch; not more than about 0.30% of a food preservative, preferably potassium sorbate; and about 26.0 to about 30.0% of cholestyramine, most preferably about 28.0%. The cholestyramine utilized may be, for example, cholestyramine resin which has been USP-approved. The total moisture content of the final composition is preferably not greater than about 4.0%, and most preferably not greater than about 2.0% of the total composition.

In another especially desirable embodiment of the invention, the cholestyramine composition further comprises an edible oil, in addition to the ingredients heretofore outlined. The edible oil may be one or more animal or vegetable-based oils or a combination thereof, with vegetable oils being preferred, and soybean oil being especially preferred. Those oils which contain unacceptable levels of cholesterol and oils which the body will convert to cholesterol should be avoided. It has been found that the edible oil improves the taste and mouth-feel of the final composition, but those skilled in the art will recognize that the oil will increase the caloric content of the composition.

In the heretofore described embodiment of the invention wherein the final composition comprises an edible oil, the following percentages of the heretofore described components on a weight basis are most preferred: grain-based product(s), about 13.0% to about 14.0%; sugar(s), about 35.0% to about 40.0%; flavoring(s), about 1.0% to about 2.0%; acid hydrolyzed starch binder, about 7.0% to about 8.0%; preservative(s), about 0.25% to about 0.30%; edible oil, most preferably soybean oil, about 12.0% to about 15.0%; cholestyramine, about 22.0% to about 26.0%, most preferably, about 24.0%; and a moisture content of about 2.0% to about 4.0%, most preferably not greater than about 2.0%. The especially preferred ingredients, e.g. rolled oats and oat bran as the grain-based product, as well as their preferred ratios, if any, are the same as those outlined for the especially preferred embodiment without an edible oil. The embodiment with an edible oil typically has more calories than the composition without the oil.

Those skilled in the art may find it possible to vary somewhat the quantity and therefore the actual weight percentages of the ingredients heretofore set forth, or to substitute certain ingredients for others, or even eliminate certain ingredients, depending upon taste preferences as well as other factors. The foregoing may be accomplished while still keeping the moisture content of the final cholestyramine composition relatively low, and thereby keeping the composition relatively more palatable as compared with currently available formulations in the art.

The term "non-baked" as it is used herein refers to a product which has been dried at or about an elevated temperature, preferably in the range of about 70° C. in a conventional or vacuum-type drying oven typically utilized in pharmaceutical operations. This is to be contrasted with conventional baking in a standard-type oven at approximately 150° C. or greater. It has been discovered that by drying the cholestyramine composition according to the various embodiments of the present invention for a period of about 16 to about 48 hours, preferably about 20 hours at a temperature of approximately 70° C., that a moisture range of less than about 11.0%, and preferably less than about 2.0 or 4.0% in the final non-baked composition can be more easily attained than if the same composition is baked conventionally at a much higher temperature for a considerably shorter period of time. It is believed the low moisture content in turn improves both the taste and mouth-feel of the final composition.

The cholestyramine composition according to the invention, including either of the especially preferred embodiments with or without one or more edible oils, will most preferably have the consistency of coarse granules similar in size, appearance and texture to that of wheat germ or granola. It is highly desirable that the coarse granules range in size from about 0.5 mm to about 3.0 mm in length, width, and height. A typical unit dosage will contain a multiple of these granules and weigh about 10.0 to about 17.0 grams, including up to about 4.0 grams of cholestyramine per dosage.

The heretofore described compositions may also be shaped in the form of croutons similar to those typically utilized in soups or salads. A unit dosage of these croutons will comprise one or more individual croutons and will weigh about 10.0 to about 17.0 grams, including up to about 4.0 grams of cholestyramine per dose. There will preferably be several, e.g. three or more, croutons per dose. It is desirable that each crouton range in size from about 0.5 cm to about 1.0 cm in length, width and height.

The embodiment heretofore described without an edible oil may also be processed into tablets that are highly palatable even when ingested without a beverage. In this embodiment of the invention, it is especially desirable to use compressible sugars, e.g. mannitol and sorbitol, as the sweetening agents in an approximate 1:1 ratio with the more conventional simple sugars, e.g. fructose powder. Compressible sugars may also be utilized in lieu of fructose powder. Those skilled in the art may find that other ratios of compressible sugar(s) and the more conventional sweeteners may yield optimal results. In any event, the total weight percentage of sweetening agent(s) in the tablet embodiments should preferably be approximately the same as heretofore set forth for the coarse granule and crouton formulations.

The chewable tablet formulations also preferably comprise magnesium stearate as a lubricating agent in an amount of from about 0.3% to about 1.0% of the final composition. Lubricating agents are often employed so that the tablets can be easily removed from the individual dies after casting and will not "stick" thereto. Another suitable lubricating agent may be, for example, staeric acid.

A single dosage of the chewable tablet formulation will typically comprise about 4.0 grams of cholestyramine. Preferably, there will be about 4 to 6 tablets per dose, with each tablet having about 1.0 to about 0.75 grams of cholestyramine.

To prepare the cholestyramine composition according to the various embodiments of the invention, the following procedures may be utilized. For the embodiments with or without oil wherein the final composition has the form of coarse granules, the separate ingredients heretofore set forth may be measured into a mixing bowl. A quantity of water is added to the dry ingredients such that the total % weight of added water is approximately 15.0 to about 17.0% based on the total weight of the resulting wet composition. Those skilled in the art may find it desirable to add more or less water during the process so as to achieve optimal mixing.

The various ingredients are blended together with suitable mixing equipment at slow or low speed to produce a substantially homogeneous mixture. The resulting wet mixture is then passed through a standard laboratory mesh screen, sizes #3 through #20 may be utilized, with size #8 being especially preferred. The resulting granules are then dried in a drying oven as heretofore outlined until the final moisture content of the composition is preferably not more than about 11.0%. It is during this drying process that the excess moisture present in the wet composition is removed.

To prepare the crouton formulations, the same procedure is followed as for the coarse granule compositions, with the following exceptions. After all ingredients are blended, the resulting wet composition is then cut or sliced into individual croutons having the dimensions heretofore set forth. The individual croutons are then dried in the manner previously outlined.

To prepare the embodiment without oil in chewable tablet form the same basic procedure is again followed, except that no edible oil is utilized in the mixture. The various components, including about 15.0 to about 17.0% weight of added water based on the total weight of the wet composition, are blended at low speed to attain a substantially homogeneous mixture. This mixture is then passed through a finer mesh screen, preferably through a #16 type mesh screen, and dried as heretofore outlined. The resulting composition is then compressed into tablets using suitable tooling well known in the art.

The following examples illustrate the various preferred embodiments of the invention, and should in no way be construed as limiting the scope thereof.

EXAMPLE 1—COARSE GRANULE FORMULATION WITH OIL

To prepare this formulation 120.0 grams of rolled oats, 110.0 grams of oat bran, 400.0 grams of USP-approved cholestyramine resin, 50.0 grams of soy polysaccharide, and 130.0 grams of pregelatinized starch were combined in a mixing bowl and mixed for 5 minutes at low speed to produce a substantially homogeneous blend. 270.0 grams (ml) of purified water was then added to this mixture, and the resulting blend was again mixed for 5 minutes at low speed until a substantially homogeneous blend resulted. 3.7 grams of potassium sorbate, 11.4 grams of cinnamon and 20.0 grams of vanilla extract were then added and the mixture was again blended at low speed for 2 minutes. To this mixture was added 230.0 grams of soybean oil and the mixture was further blended at low speed for 2 minutes. 593.0 grams of fructose powder was added and blended at low speed for five minutes. The resulting wet formulation was then passed through a #8 mesh screen and dried in an oven for 20 hours at 70° C. the dried granulation was again passed through a #8 mesh screen and separated into 100 dosage units. Each dosage unit weighed about 16.0 to 18.0 grams and contained approximately 4.0 grams of cholestyramine. Each dosage had approximately 50.0 calories. The resulting moisture content of the dried granulation was in the 2.0 to 4.0% range. The final product had the look, texture, taste and mouth-feel very similar to that of wheat germ or granola, and was extremely good-tasting even when consumed in its dry state.

EXAMPLE 2—COARSE GRANULE FORMULATION WITHOUT OIL

The same procedure was followed as in Example 1, except that no soybean oil was utilized. The final product was separated into 100 dosage units. Each dosage unit weighed about 14.0 to 15.0 grams and contained about 4.0 grams of cholestyramine. Each dosage unit had approximately 30.0 calories. The final product was also very similar to wheat germ, with a highly acceptable taste and mouth-feel. The resulting moisture content of the dried granulation was in the 2.0 to 4.0% range.

EXAMPLE 3—CROUTON FORMULATION WITH OIL

The same procedure was followed as in Example 1, except that the resulting wet composition was cut into croutons. The final product was separated into 100 dosage units, with each dosage unit containing on average about 5 croutons. Each dosage unit weighed from about 16.0 to 18.0 grams and contained about 4.0 grams of cholestyramine. The caloric content of one dosage unit was approximately 50.0 calories. The final product was pleasant tasting and had a moisture content in the 2.0 to 4.0% range.

EXAMPLE 4—CROUTON FORMULATION WITHOUT OIL

The same procedure was followed as in Example 3, except that no edible oil was utilized in the formulation. Each dosage unit weighed about 14.0 to about 15.0 grams and contained about 4.0 grams of cholestyramine. The caloric content of a single dosage unit was about 30.0 calories. The final product was highly palatable and had a moisture content in the 2.0 to 4.0% range.

EXAMPLE 5—CHEWABLE TABLET FORMULATION (WITHOUT OIL)

The same procedure was followed as in Example 1, but with the following differences. No soybean oil was utilized, and 593.0 grams of compressible sugars (a combination of sorbitol, mannitol, and two other compressible sugars marketed under the tradenames SWEETREX and DI-PAC) were substituted for the fructose powder, and 7.0 grams of magnesium stearate were added as a lubricant. A finer mesh screen #16 was substituted for the #8 screen utilized in Example 1. After the dried formulation was passed through the #16 screen, the product was compressed into tablets using standard laboratory tools. The resulting moisture content of the tablets was in the 2.0% to 4.0% range. Each dose had approximately 30.0 calories, and contained about 4.0 grams of cholestyramine. Each dose averaged 4 to 6 tablets and contained 1.0 to 0.75 grams of cholestyramine per tablet.

Also included as part of the invention is a method for lowering or controlling high blood cholesterol levels in humans. This method comprises administering a therapeutically effective quantity of any one of the embodiments of the cholestyramine composition set forth herein. The cholestyramine composition which is ingested should have a moisture content not exceeding about 11.0%, preferably not exceeding about 4.0%, and most preferably not exceeding about 2.0%. By lowering the moisture content the taste of the composition will be improved, thereby permitting the patient to more easily adhere to a regimen of treatment.

An especially preferred method of cholestyramine treatment would comprise ingesting one of the dosage forms of coarse granule formulation set forth in Examples 1 and 2, the crouton formulations of Examples 3 and 4, or the chewable tablet form in Example 5 on a regular basis. Each dosage form would contain about 4.0 grams of cholestyramine, and could be taken from 1 to 6 times daily, or as prescribed by a physician. Each dosage form could be ingested as is, that is without being accompanied by a beverage.

The coarse granule composition could also be mixed with yogurt or other low-fat dairy and nondairy products and taken as a snack. If desired, the chewable tablet formulation could be followed by a liquid.

Although the invention has been described in detail in its various embodiments for the purpose of illustration, it is to be understood that such description is solely for that purpose and that variations may be made therein by those skilled in the art without departing from the spirit and scope of the invention as set forth in the following claims.

We claim:

1. An edible, non-baked composition suitable for use in lowering or controlling blood cholesterol levels in humans, comprising a therapeutically effective quantity of cholestyramine in stable admixture with at least one flour selected from the group consisting of wheat, corn, oats and their brans; and one or more simple, double or complex sugars; said composition having a total moisture content not exceeding about 11.0% by total weight, said composition further being in the form of dried granules, croutons, or tablets.

2. The composition as claimed in claim 1, wherein said total moisture content does not exceed about 4.0% by weight.

3. The composition as claimed in claim 2, wherein said total moisture content does not exceed about 2.0% by weight.

4. The composition as claimed in claim 1, further comprising a starch binder.

5. The composition as claimed in claim 4, further comprising at least one flavoring agent and at least one food preservative.

6. The composition as claimed in claim 5, further comprising at least one edible oil.

7. The composition as claimed in claim 5, wherein said total moisture content does not exceed about 4.0% by weight.

8. The composition as claimed in claim 5, wherein said total moisture content does not exceed about 2.0% by weight.

9. A method of controlling or lowering blood cholesterol levels in humans which comprises administering to a patient the cholestyramine composition of claim 1.

10. An edible, non-baked composition, comprising a therapeutically effective quantity of cholestyramine in stable admixture with a combination of rolled oats and oat bran, fructose powder and soy polysaccharide, vanilla extract and cinnamon, pregelatinized starch, potassium sorbate, and soybean oil, said composition having a total moisture content not exceeding about 4.0% by weight.

11. The composition as claimed in claim 10, comprising on a weight basis from about 10.0 to about 20.0% of a combination of rolled oats and oat bran, about 30.0 to about 40.0% of a combination of soy polysaccharide and fructose powder, about 0.5 to about 2.5% of a combination of vanilla extract and cinnamon, about 5.0 to about 10.0% of pregelatinized starch, about 0.1 to about 1.0% of potassium sorbate, about 10.0 to about 15.0% of soybean oil, and about 20.0 to about 30.0% of cholestyramine.

12. The composition as claimed in claim 11, wherein said composition is in the form of coarse granules or croutons.

13. The composition as claimed in claim 12, wherein said composition has a total moisture content not exceeding about 2.0% by weight.

14. The composition as claimed in claim 12, comprising on a weight basis from about 13.0 to about 14.0% of a combination of rolled oats and oat bran, about 35.0 to about 40.0% of fructose powder and soy polysaccharide, about 1.0 to about 2.0% of vanilla extract and cinnamon, about 7.0% to about 8.0% of pregelatinized starch, about 0.25% to about 0.30% of potassium sorbate, about 12.0% to about 15.0% of soybean oil, and about 22.0% to about 26.0% of cholestyramine.

15. The composition as claimed in claim 10, wherein said composition has a total moisture content not exceeding about 2.0% by weight.

16. An edible, non-baked cholestyramine composition, comprising on a weight basis from about 7.0 to about 20.0% of a combination of rolled oats and oat bran, about 40.0 to about 50.0% of fructose powder and soy polysaccharide, about 0.5 to about 3.0% of vanilla extract and cinnamon, about 5.0 to about 10.0% of pregelatinized starch, and about 0.1 to about 1.0% of potassium sorbate, and about 25.0 to about 35.0% cholestyramine, said composition having a total moisture content not exceeding about 4.0% by weight.

17. The composition as claimed in claim 16, further comprising magnesium stearate in an amount of from about 0.3 to about 1.0% based on the weight of the total composition, said composition being in chewable tablet form.

18. The composition as claimed in claim 16, wherein said composition is in coarse granule or crouton form.

19. The composition as claimed in claim 16, wherein said composition has a total moisture content not exceeding about 2.0% by weight.

20. An edible, non-baked cholestyramine composition, comprising on a weight basis from about 7.0 to about 20.0% of a combination of rolled oats and oat bran, about 40.0 to about 50.0% of compressible sugars and soy polysaccharide, about 0.5 to about 10.0% of pregelatinized starch, about 0.1 to about 1.0% of potassium sorbate, and about 25.0 to about 35.0% cholestyramine, said composition further comprising magnesium stearate in an amount of from about 0.3 to about 1.0%, said composition being in chewable tablet form and having a total moisture content not exceeding about 4.0% by weight.

21. A method of lowering or controlling blood cholesterol levels in humans which comprises administering a therapeutically effective dosage of an edible, non-baked composition comprising cholestyramine in stable admixture with rolled oats and oat bran, fructose powder and soy polysaccharide, vanilla extract and cinnamon, pregelatinized starch, potassium sorbate, the total moisture content of said composition not exceeding about 11.0% by total weight.

22. An edible, non-baked cholestyramine composition, comprising a therapeutically effective quantity of cholestyramine in stable admixture with a combination of rolled oats and oat bran, fructose powder and soy polysaccharide, vanilla extract and cinnamon, pregelatinized starch, potassium sorbate, said composition having a total moisture content not exceeding about 11.0% by weight.

23. The composition as claimed in claim 22, further comprising soybean oil.

* * * * *